United States Patent [19]
Gelman

[11] Patent Number: 5,031,419
[45] Date of Patent: Jul. 16, 1991

[54] PERFUMED EARRING CLASP

[76] Inventor: Emanuel Gelman, 2467 Rte. 10E, Bldg. #2 - Apt 48, Morris Plains, N.J. 07950

[21] Appl. No.: 498,733

[22] Filed: Mar. 26, 1990

[51] Int. Cl.$^5$ .............................................. A44C 7/00
[52] U.S. Cl. .......................................... 63/12; 24/705; 63/DIG. 2
[58] Field of Search ................... 63/12, 13, DIG. 2; 239/36, 53; 24/705

[56] References Cited

U.S. PATENT DOCUMENTS

| | | | |
|---|---|---|---|
| 477,217 | 6/1892 | McCoy | 63/DIG. 2 |
| 1,324,466 | 12/1919 | Pirro | 24/705 |
| 2,740,662 | 4/1956 | Scott | 63/12 X |
| 4,056,951 | 11/1977 | Black | 63/DIG. 2 |
| 4,353,370 | 10/1982 | Evans | 63/12 X |
| 4,874,129 | 10/1989 | DiSapio et al. | 239/36 |

FOREIGN PATENT DOCUMENTS

| | | | |
|---|---|---|---|
| 524993 | 9/1921 | France | 24/705 |
| 599124 | 3/1948 | United Kingdom | 63/DIG. 2 |

*Primary Examiner*—James R. Brittain
*Attorney, Agent, or Firm*—Iman Abdallah

[57] ABSTRACT

An earring clasp for pierced-ear type earrings that provides means for disposing a perfuming agent substantially near or in contact with the ear lobe of the wearer. The earring clasp is formed having a first disk member, a second disk member and a body of sorbent material sandwiched between the first and second disk members. A plurality of air holes extend transversely through the clasp to permit air flow about the wearer's ear lobe. In one embodiment of the earring clasp, the first disk member is disposed adjacent to the wearer's ear lobe and is formed from a fluid pervious material to permit capillary transmission of a perfuming agent disposed on the sorbent material.

4 Claims, 1 Drawing Sheet

PERFUMED EARRING CLASP

BACKGROUND OF THE INVENTION

The present invention generally relates to perfumed ear attachments. More specifically, the present invention relates to clasp means for pierced-ear type ear attachments that can receive and transmit perfume to the skin of the wearer.

Perfumed earrings of various types have been disclosed in the prior art. In U.S. Pat. No. 1,267,067 to Flagg a perfumed ear attachment is disclosed comprising a perforated receptacle that encloses a perfume-carrying medium. In U.S. Pat. No. 1,625,375 to Reyes an ear attachment is disclosed wherein perfume is disposed in a vial having a perforated cap. In U.S. Pat. No. 2,058,274 to Vivaudou et al. a perfumed earring is disclosed wherein perfumed particles are disposed in the earring. U.S. Pat. No. 2,471,949 to Gilowitz discloses an aromatic earring having a wick that communicates with perfume disposed within an ornamental receptacle. These earlier inventions were directed to providing perfuming means for the clip-on type earrings. A perfumed pierced-ear type earring is disclosed in U.S. Pat. No. 4,056,951 to Black.

A particular disadvantage of the perfumed earrings of the prior art is that they fail to provide means for the perfuming agent to come into contact with the skin of the wearer. The scent provided by a perfuming agent is affected by its chemical reaction with the human body. For this reason the same perfuming agent will emit a different fragrance when worn by different people. Also, the perfumed earrings of the prior art require that the ornamental portion of the earring be formed as a hollow member for receipt of the perfuming agent which prohibits the provision of a perfumed earring having a flat or petite body structure.

Furthermore, in the pierced-ear type earrings the detent sleeve oftentimes is formed as a cylindrical disk which lays flatly against the ear lobe. Pierced ears often become infected and the disk construction of the detent sleeve prevents the free flow of air about an infected ear lobe which would facilitate healing. Thus there remains a need in the art for an earring that will bring a perfuming agent in contact with the skin of the wearer that is suitable for use with earrings having a flat or petite structure and that further provides means for air flow about an infected pierced ear to promote healing.

SUMMARY OF THE INVENTION

The present invention discloses a clasp for pierced-ear type earrings comprising an earring post attachment member which engages the post of the ornamental portion and is formed by a pair of disk members having sorbent material sandwiched between the disk members, the sorbent material being provided for receipt of a perfuming agent. In a preferred embodiment of the earring the post attachment member includes a plurality of air holes which extend through the respective disk members and the sorbent material to provide means for air flow about the pierced ear lobe. The disk member disposed adjacent to the ear lobe is formed from a fluid pervious material to permit contact of the perfuming agent with the skin of the user.

An object of the present invention is to provide an earring clasp for pierced-ear type earrings having sorbent material that can be selectively perfumed by the wearer or marketed in various scents.

Another object of this invention is to provide an earring clasp for pierced-ear type earrings that brings a perfuming agent in contact with the skin of the wearer.

It is also an object of the present invention to provide an earring clasp that permits air flow about the wearer's ear lobe.

A further object of the present invention is to provide earring clasping means that can be utilized with any ornamental style of post type earrings.

These and other objects and advantages of the present invention will be apparent to those skilled in the art from the following description of a preferred embodiment, drawings and appended claims.

DESCRIPTION OF A PREFERRED EMBODIMENT

Figure 1:
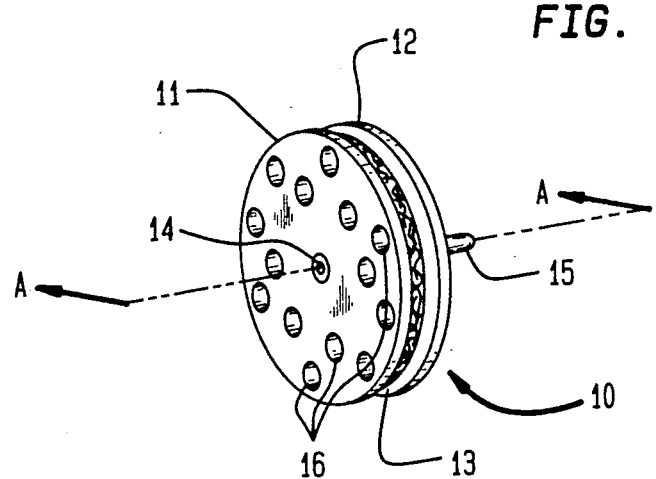
FIG. 1 is a side perspective view of the earring clasp of the present invention.

FIG. 1 illustrates in a side perspective view the earring clasp 10 of the present invention. Earring clasp 10 generally comprises a a three-layered body including a first clasp disk 11, a second clasp disk 12 and a body of sorbent material 13 sandwiched between said first disk 11 and said second disk 12. The first clasp disk 11 is preferably formed from a fluid pervious material to facilitate transmission of a perfuming agent disposed on the sorbent material 13 from the clasp 10 to the skin of the wearer as hereinafter described in greater detail. Clasp 10 includes an earring post receptacle 14 comprising a central bore extending through the first disk 11, the body of sorbent material 13 and the second disk 12. A clasp handle 15 is fixedly attached to the outside surface of the second disk 12 in horizontal alignment with the post receptacle 14 to facilitate manual gripping of the clasp 10 during attachment of the clasp 10 to the post of an earring. A plurality of air holes 16 are disposed about the post receptacle 14 which extend completely through the various layers 11, 12, 13 of the clasp 10.

Figure 2:
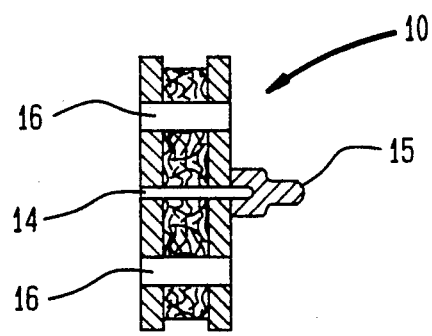
FIG. 2 is a plan cross-sectional view taken along line A—A of FIG. 1.

FIG. 2 illustrates a cross-sectional view of the clasp 10 wherein it can be better seen that the air holes 16 traverse the respective layers 11, 12, 13 of the clasp 10. The central bore defining the post receptacle 14 extends into the clasp handle 15 for a marginal distance. The clasp handle 15 is shown to include a central bore coextensive with the post receptacle 14, however, the bore of the clasp handle 15 may be alternatively formed in a manner to resiliently engage the end of a post inserted therein.

Figure 3:
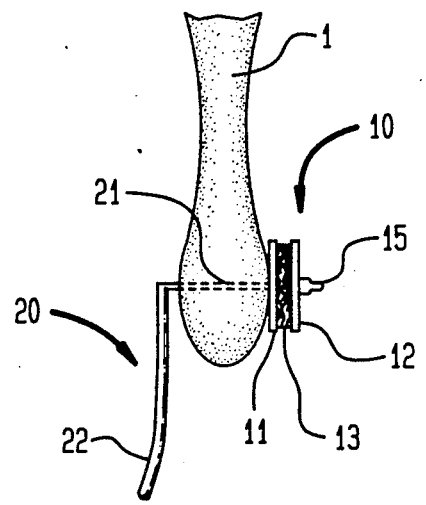
FIG 3 is a side plan view of the earring clasp of the present invention shown attached to a pierced-ear type earring disposed in an ear lobe.

Referring now to FIG. 3, it can be seen that when the earring clasp 10 of the present invention is attached to the post 21 of a pierced-ear type earring 20, the ornamental portion 22 of the earring 20 is disposed to the outside of the ear lobe 1 as heretofore known and understood, and the earring clasp 10 is disposed to the inside of the ear lobe 1 having the first disk 11 laying in contact with the ear lobe 1.

A primary advantage of the earring clasp 10 of the present invention is the provision of integrally formed means to permit a perfuming agent to come into contact with the skin of the wearer. As seen in FIG. 3 when the earring clasp 10 is attached to the earring post 21, the first disk 11 lays against a portion of the wearer's ear lobe 1. A liquid perfuming agent disposed on the sorbent material 13 moves by capillary action from the sorbent material 13 through the fluid pervious first clasp disk 11 to contact the wearer's ear lobe 1.

It is within the scope and spirit of the present invention that the first clasp disk 11 and second clasp disk 12 may be formed of a variety of materials, including an impervious plastic. In such a construction of the clasp 10 the air about the wearer's ear lobe 1 may be scented without the perfuming agent coming into contact with the wearer's skin which may be desirable if the wearer's ear lobe 1 is infected or sensitive to a particular perfuming agent. It should also be understood from the foregoing that the clasp 10 of the present invention may be perfumed prior to marketing or may be provided to the user unscented so that different perfuming agents may be applied to the sorbent material 13 as desired by the wearer.

Therefore, in the view of the foregoing I claim:

1. Earring clasping means for pierced-ear type earrings having an ornamental portion and a post extending from said ornamental portion to engage a hole in a wearer's earlobe, said clasping means comprising
    an earring post attachment member formed by a pair of parallel disk members having sorbent material sandwiched between said disk members, the sorbent material being provided for receipt of a perfuming agent, said post attachment member having a centrally disposed bore extending transversely through said post attachment member which engages the post of the pierced-ear type earring,
    said post attachment member including at least one air hole extending through the respective disk members and the sorbent material to provide means for air flow about the hole of the wearer's earlobe, said disk members comprising a first disk member disposable adjacent to the wearer's earlobe and a second disk member having a handle fixedly attached to an outside surface of said second disk member, said first disk member being formed from fluid pervious material for capillary transission of a perfuming agent disposed on said sorbent material from said sorbent material to the wearer's earlobe.

2. An earring comprising
    an ornamental portion having a forward side and a rearward side;
    a post extending from the rearward side of said ornamental portion; and
    earring clasping means as described in claim 1.

3. Clasping means for ornamental devices of the type having an ornamental portion and a post extending from said ornamental portion to selectively engage a hole in a wearer's body, said clasping means comprising
    a post attachment member formed by a first flat disk member and a second flat disk members disposed in parallel alignment having a body of sorbent material disposed therebetween,
    said first and second disk members and said body of sorbent material having a plurality of displaced openings extending transversely through said disk members and said body of sorbent material in parallel alignment,
    said first disk member being formed from fluid pervious material and said second disk member being formed from fluid impervious material,
    said first disk member being disposable adjacent to the wearer's earlobe for capillary transmission of a perfuming agent from said body of sorbent material through said first disk member to the wearer's earlobe,
    said post attachment member having a bore extending transversely through said post attachment member, said post being receivable in sliding frictional engagement within said bore.

4. Clasping means as described in claim 3 having a handle fixedly attached to an outside surface of said second disk member.

* * * * *